United States Patent [19]

Kikuchi et al.

[11] Patent Number: 5,029,475
[45] Date of Patent: Jul. 9, 1991

[54] MEASURING SPATIAL DISTRIBUTION OF SPACINGS BETWEEN POINT SCATTERERS

[75] Inventors: Tsuneo Kikuchi; Shogo Kiryu, both of Tsukuba, Japan

[73] Assignee: Agency of Industrial Science and Technology, Tokyo, Japan

[21] Appl. No.: 498,120

[22] Filed: Mar. 23, 1990

[30] Foreign Application Priority Data

May 22, 1989 [JP] Japan .................................. 1-128538

[51] Int. Cl.$^5$ ............................................... G01N 29/00
[52] U.S. Cl. ................................ 73/602; 128/661.03; 364/413.25
[58] Field of Search .................... 73/602; 364/413.25; 128/660.07, 661.03

[56] References Cited

U.S. PATENT DOCUMENTS 4,545,250 10/1985 Miwa ...................................... 73/602
4,655,228 4/1987 Shimura et al. ........................ 73/602
4,789,933 12/1988 Chen et al. ...................... 364/413.13
4,855,911 8/1989 Lele et al. ............................. 73/602

OTHER PUBLICATIONS

*Peritoneoscopy*, Kono et al, No. 8, May 1988, pp. 87–90.

*Primary Examiner*—John E. Chapman
*Attorney, Agent, or Firm*—Armstrong, Nikaido, Marmelstein, Kubovcik & Murray

[57] ABSTRACT

Method of and apparatus for measuring a space distribution of spacings between point scatterers. An ultrasonic wave is applied to an ultrasonic scattering medium which is an aggregation of point scatterers. Ultrasonic waves, scattered from the medium, are converted into an electric signal. The shape of a power spectrum of the electric signal is determined. A fractal analysis is effected so as to determine a fractal dimension and self-similarity with respect to the power spectrum shape. A spatial distribution of a structural inhomogeneity of the scattering medium is measured in accordance with results of the fractal analysis.

2 Claims, 10 Drawing Sheets

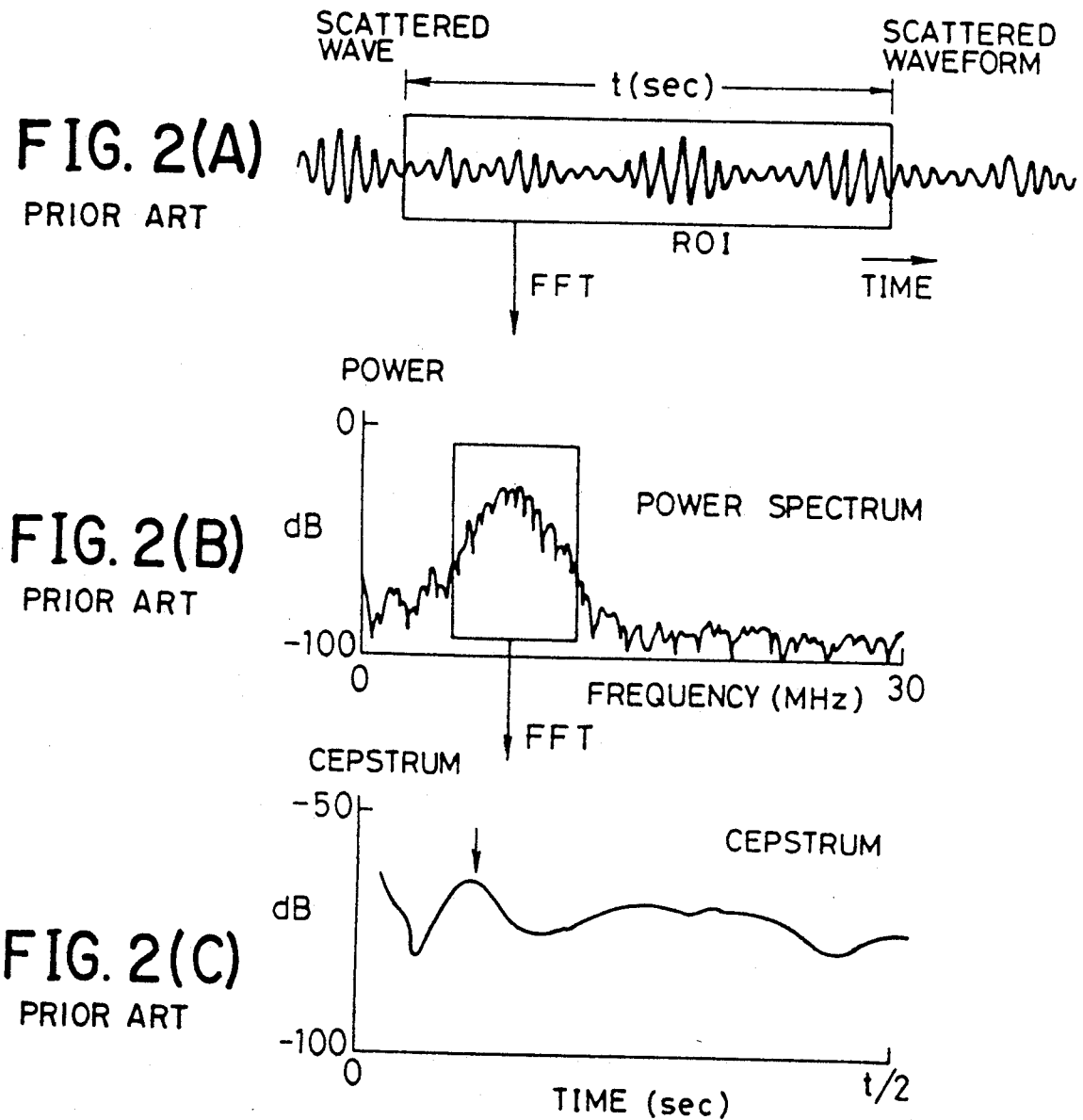

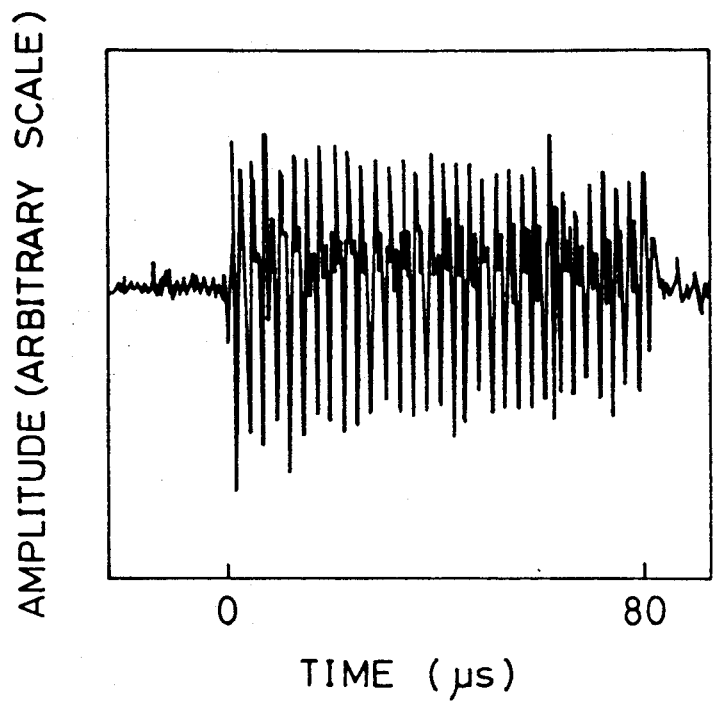
F I G. 9A
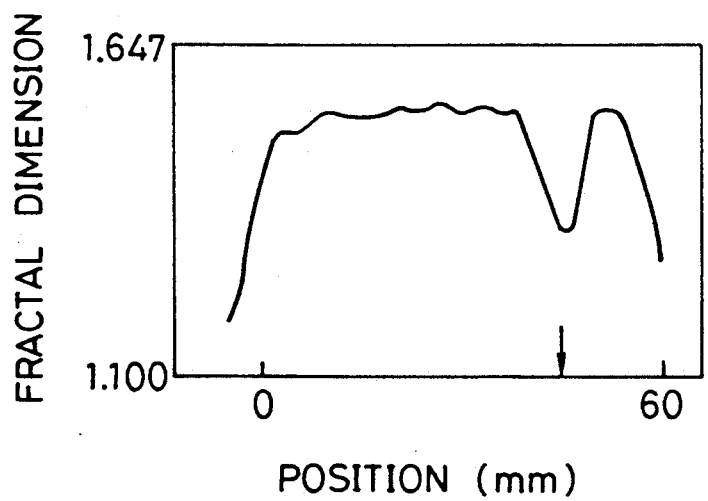
F I G. 9B

MEASURING SPATIAL DISTRIBUTION OF SPACINGS BETWEEN POINT SCATTERERS

FIELD OF THE INVENTION

The present invention relates to the art of measuring an inhomogeneous space distribution of an ultrasonic scattering medium composed of point scatterers, this technique being used, for example, in an ultrasonic diagnosis of living tissues in a clinical medicine (for example, to effect an early detection of a tumor or the like produced in a human organ), an ultrasonic nondestructive test of composite materials of an inhomogeneous structure in various industries, and an ultrasonic marine inspection at those sea areas where there exist many floating or suspended matters adversely affecting the measurement.

DESCRIPTION OF THE PRIOR ART

In conventional ultrasonic measurement techniques used in the above fields, the spatial distribution of the scattering medium is measured by the amplitude of the ultrasonic scattered waves reflected from the scattering medium. There have been several cases where the scattering medium is regarded as an aggregation of point scatterers, so that the spatial distribution of the aggregation of point scatters is analyzed. However, here, a cepstrum method which has been employed in a medical diagnosis as one example of study will now be described. A circuitry of a measurement apparatus employing such a cepstrum method is shown in FIG. 1.

The measurement apparatus employing the cepstrum method comprises an ultrasonic transducer drive device 1, a transmitting/receiving ultrasonic transducer 2, an ultrasonic receiver 3, power spectrum calculating devices 4, and a result display device 5.

A pulse voltage produced by the ultrasonic transducer drive device 1 is applied to the transmitting-/receiving ultrasonic transducer 2. This pulse voltage is converted into mechanical vibration and is radiated in the space as a ultrasonic wave, and this ultrasonic wave is scattered by a sample 6 which is a scattering medium composed of an aggregation point scatterers. The frequency of the ultrasonic wave varies according to the measurement purpose. For example, in the case of the measurement of a sample of biotissue, this frequency is usually not higher than 10 MHz. In some cases, depending on the purpose, a transducer capable of focusing an ultrasonic beam is used as the transmitting/receiving ultrasonic transducer 2. In the case of measuring backscattering waves from the scattering medium, as in the above measurement, the single transducer also performs the function of transmitting and receiving the wave. Therefore, the ultrasonic waves scattered by the scattering medium again reach the transducer, and the mechanical vibration is converted into an electrical signal. The electric signal resulting from the conversion through the transducer is inputted into the ultrasonic receiver 3, and is subjected to amplification, etc., if necessary. Further, the electric signal is subjected to an analog-to-digital (A/D) conversion, and is inputted into the power spectrum calculating device 4 where the power spectrum of the received wave is calculated. Further, in order to find the characteristics of the shape of this power spectrum, a fast Fourier transform (FFT) is carried out at the power spectrum calculating device 4 to thereby obtain a cepstrum. The (thus) obtained cepstrum is displayed in the display device 5 having either a display screen or a plotter. This method is disclosed by Kono et al. (Peritoneoscopy, No. 8, May 1988). In this method, as shown in FIG. 1, the time waveform is twice subjected to a fast Fourier transform (FFT) to obtain the cepstrum, and the characteristics of the shape of the power spectrum are extracted from it. FIG. 2 shows the process of the analysis by this method. The cepstrum waveform obtained by this method has a peak (indicated by arrow in FIG. 2) at a certain point on the time base. If this peak position is represented by $\tau$, the spacing a between the point scatterers is expressed by the following formula:

$$a = \tau \times C/2$$

where C represents the acoustic (sound) velocity.

Thus, in the conventional method, the average spacing between the point scatterers in the ultrasonic scattering medium is determined on the basis of the peak position of the cepstrum waveform.

However, with the above conventional measurement method, when the spacing between the point scatterers constituting the ultrasonic scattering medium is less than the wavelength of the scattered wave, it has been impossible to numerically measure the spatial distribution of the point scatterers (the irregularity of the spacing between the point scatterers). In other words, it has been impossible to numerically measure the inhomogeneity (non-uniformity) of the ultrasonic scattering medium.

SUMMARY OF THE INVENTION

It is therefore an object of this invention to provide a method of and an apparatus for measuring a space distribution of spacings between point scatterers.

According to one aspect of the present invention, there is provided a method of measuring a space distribution of spacings between point scatterers, comprising the steps of:

applying an ultrasonic wave to an ultrasonic scattering medium which is an aggregation of point scatterers;

converting ultrasonic waves, scattered from the medium, into an electric signal;

determining the shape of a power spectrum of the electric signal;

effecting a fractal analysis so as to determine a fractal dimension and a self-similarity with respect to the power spectrum shape; and measuring a spatial distribution of a structural inhomogeneity of the scattering medium in accordance with results of the fractal analysis.

According to another aspect of the present invention, there is provided an apparatus for measuring a space distribution of spacings between point scatterers, comprising:

a transmitting/receiving ultrasonic transducer;

means for driving the ultrasonic transducer to cause the vibration to apply an ultrasonic wave to an ultrasonic scattering medium, which is an aggregation of point scatterers, so that the transducer receives scattered waves from the scattering medium and outputs an electric signal representative of the scattered waves;

ultrasonic receiver means for converting the electric signal from an analog form into a digital form;

power spectrum calculating means responsive to a digital output signal from the ultrasonic receiver means so as to calculate the shape of a power spectrum of the scattered waves; and fractal analysis means for effecting a fractal analysis of the power spectrum shape.

In order to overcome the above-mentioned problems of the prior art, in the present invention, the fractal analysis of the power spectrum shape is used as means for numerically estimating the power spectrum shape, instead of using the conventional method of finding a cepstrum.

In a graphic fractal analysis, it is known that the main estimate quantities include "fractal dimension", "self-similarity", etc. (For example, "Fractical-Based Analysis of 3D Natural Shapes and Its Application to Terrain Modeling"; Yokoya et al., Journal of Electronic Information Communication Society, Vol. J70-D, No. 12, p. 2605–2614, 1987, in Japanese).

The fractal theory will now be described briefly. A fractal means that even if the scale is changed, a statistical nature of the original curve is preserved. In a mathematically strict sense, such nature (fractal nature) is preserved if the scale ranges from infinity to the infinitesimal. However, in the natural world, generally, curves whose fractal nature is preserved in a limitless range of the scale do not exist. Therefore, the fractal nature should be discussed in a certain limited range of the scale.

In the present invention, attention has been paid to two estimate quantities, that is, (1) the fractal dimension and (2) self-similarity, and the two estimate quantities have been determined according to the definition of the fractal Brownian function. The fractal Brownian function is one of the fractal models to characterize the shape of the original curve.

The procedure of one example of a fractal analysis will now be described with reference to graphs shown in FIGS. 3A and 3B.

(1) The abscissa axis of a waveform (FIG. 3A) to be analyzed is divided by a certain scale df.

(2) With respect to df, the following calculations are made:

$$\log |e[A(f+df) - A(f)]| - H \cdot \log |df| = \log C \quad (2.1)$$

$$D = 2 - H \quad (2.2)$$

where the function e [ ] means that the average is taken over all the regions with respect to the certain df.

(3) The above procedure is repeated while varying the scale df.

Using the formula (2.1) as a function of df, a log-log plot is made, as shown in FIG. 3B. That portion or region of df which can be regarded as a straight line in FIG. 3B is "a scale range" in which the curve of FIG. 3A can be regarded as a fractal. From FIG. 3B, the following two quantities are determined.

FRACTAL DIMENSION

The fractal dimension D is determined from the slope H of the above straight region, using the formula (2.2). In a two-dimensional plane figure, the fractal dimension takes a real value between the value "1" and the value "2". It can be understood that if this value is closer to "1", the complexities of the original curve are less (that is, the original graph is close to a straight line), and that if this value is closer to "2", the complexities of the original graph is greater (that is, the original curve is close to a plane).

SELF-SIMILARITY

Next, the linearity of this straight region, that is, a correlation factor obtained when a least square method of this region is effected, is defined as the self-similarity. This self-similarity is a numerical value representing the degree of the fractal nature of the original curve, that is, the validity of estimate by a fractal Brownian function. The self-similarity is in the range of between the value "0" and the value "1", and if this value is closer to "1", the original curve becomes perfect fractal. In contrast, if this value is closer to "0", the fractal nature of the original curve is low.

In the present invention, by performing the above fractal analysis with respect to the power spectrum shape of the ultrasonic scattered wave, the measurement of the irregular space distribution of the spacing between the point scatterers (which could not be made by the conventional ultrasonic measurement techniques) can be carried out.

These and other objects of the present invention, together with the features and advantages thereof, will become apparent from the following detailed specification, when considered in conjunction with the accompanying drawings in which applicable reference numerals have been carried forward.

BRIEF DESCRIPTION OF THE DRAWINGS

FIG. 2 is an illustration of waveforms, showing the analysis process of a cepstrum method;

FIGS. 9A to 9D are views similar to FIGS. 8A to 8D, respectively, but are related to the sample of FIG. 7.

DETAILED DESCRIPTION OF PREFERRED EMBODIMENTS

Figure 1:
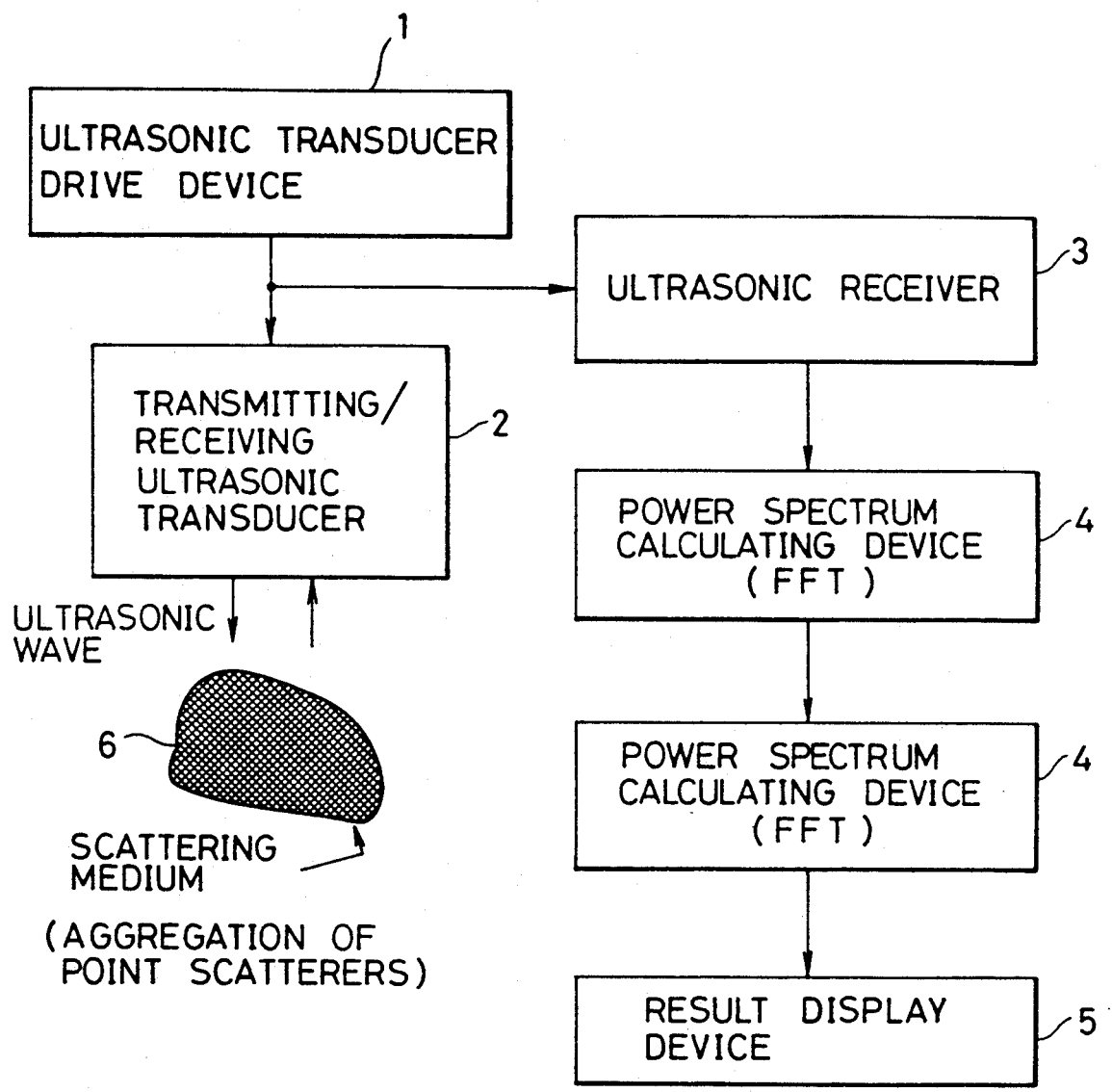
FIG. 1 is a block diagram of the circuitry of the conventional measurement apparatus.
Figure 3A:
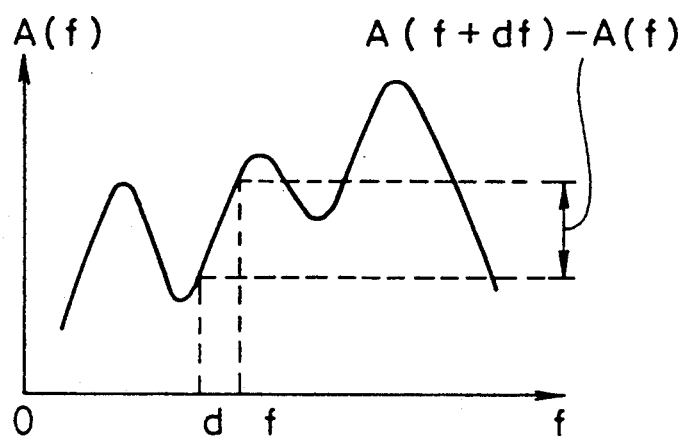
FIG. 3A is an illustration of a waveform to be subjected to a fractal analysis.
Figure 3B:
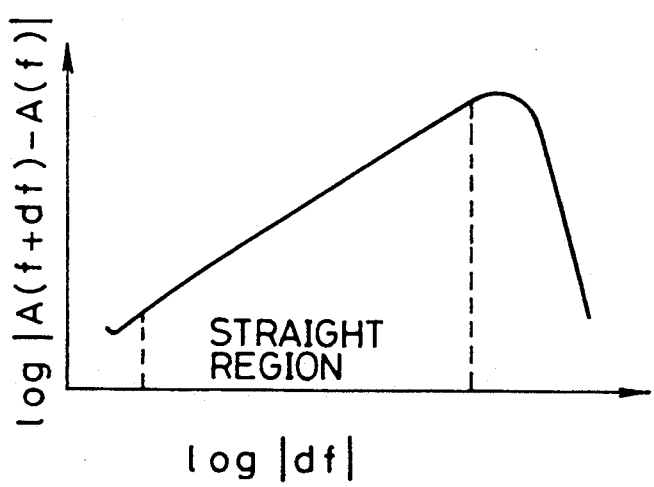
FIG. 3B is an illustration of a waveform obtained by a fractal Brownian function.
Figure 4:
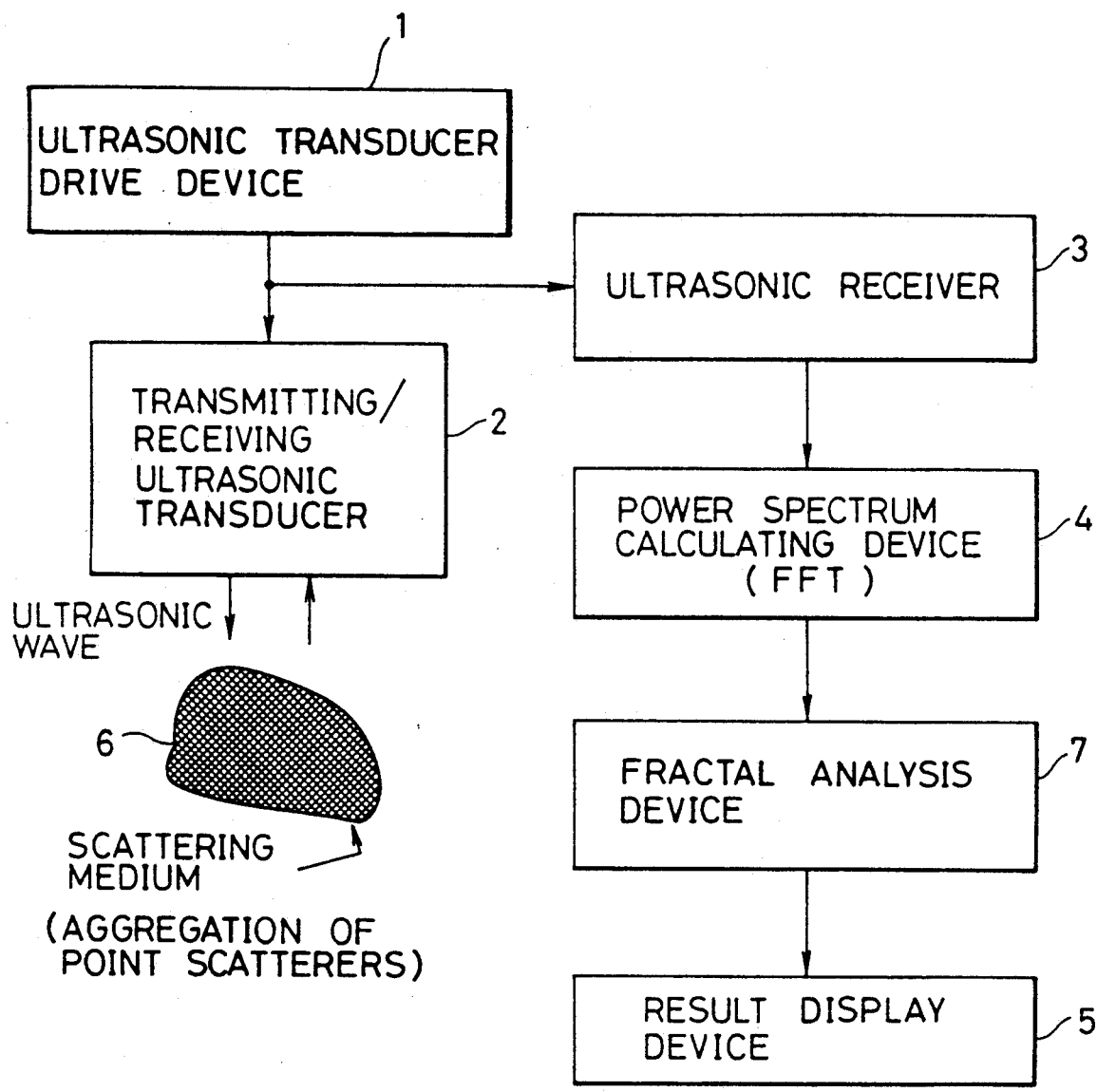
FIG. 4 is a block diagram of a circuitry of a measurement apparatus according to the present invention.

FIG. 4 shows a block diagram of one preferred embodiment of a measurement apparatus of the present invention. A main difference between this apparatus and the conventional apparatus of FIG. 1 is that the former is provided with a fractal analysis device 7 for performing a fractal analysis of the shape of a power spectrum obtained by a power spectrum calculating device 4 and for numerically calculating a fractal dimension and the self-similarity. In order to improve the relative precision of the intervals between scatterers, an ultrasonic transducer 2 used in this embodiment is of the non-focusing type having a diameter of 1 inch and having a relatively low center frequency (frequency: 0.5 MHz; underwater wavelength: 3 mm). A signal, detected and subjected to analog-to-digital (A/D) conversion by an ultrasonic receiver 3, is fed to the power spectrum calculating device (FFT device) 4. A time window is sequentially moved along the time waveform by the power spectrum calculating device 4, and the power spectrum of the waveform in each window is calculated. Then, the fractal dimension of the power spectrum as well as the self-similarity of the power spectrum is calculated by the fractal analysis device 7. In this example, the analysis was conducted, with the width of the time window being 10 μs and with the amount of movement of the window being 2 μs. 10 μs of the window width corresponds to 7.5 mm in the real space.

Figure 5:
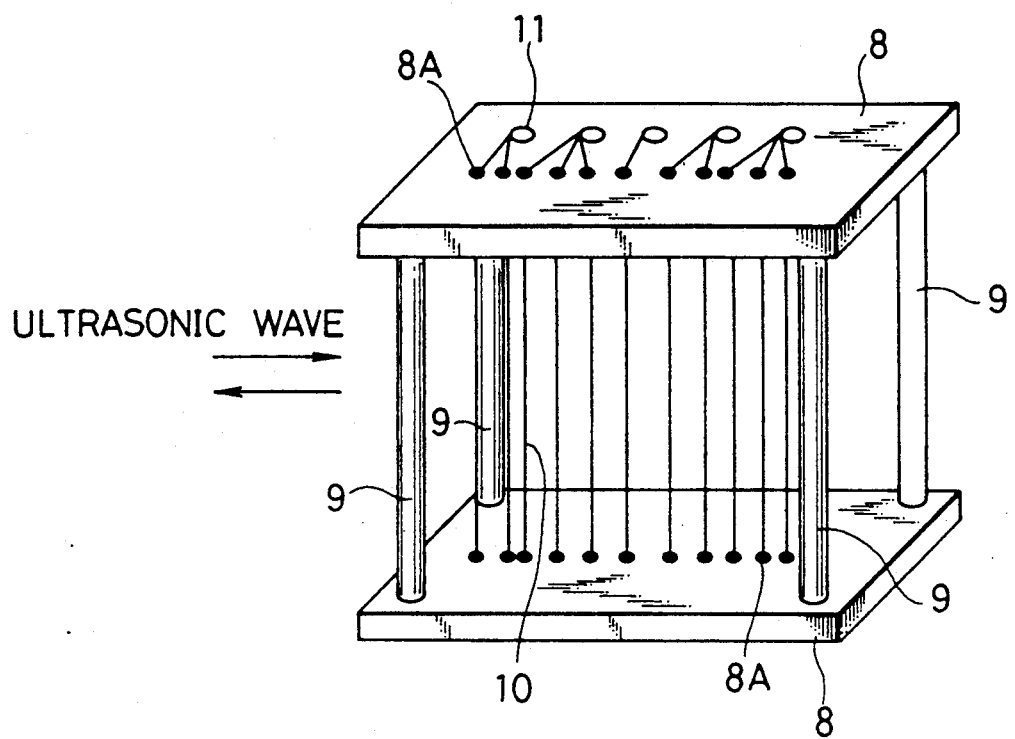
FIG. 5 is a perspective view of a sample.

As an ultrasonic scattering sample, there were used materials having a diameter small enough relative to the wavelength and having a low scattering coefficient. In this example, the ultrasonic scattering sample comprised a group of nylon wires having a diameter of 0.1 mm. As shown in FIG. 5, a support member for holding the ultrasonic scattering sample comprised two stainless steel plates 8 of a square shape (10 cm × 10 cm) which are fixedly held by brass rods 9 in opposed relation to each other and are spaced a distance of 10 cm from each other. A number of small apertures 8A are formed through each of the stainless steel plates 8. The nylon wires 10 are passed through the respective apertures 8A in each plate 8, and are fixed to the plates 8 by screws 11. Thus, the predetermined number of nylon wires 10 are fixed at predetermined intervals.

Measurements were conducted with respect to the following two samples which were different in the interval distribution of the nylon wires.

SAMPLE 1

This sample consisting of the group of scatterers had variations in the interval between the scatterers so that the scatterer spacing distribution had space variations.

Figure 6:
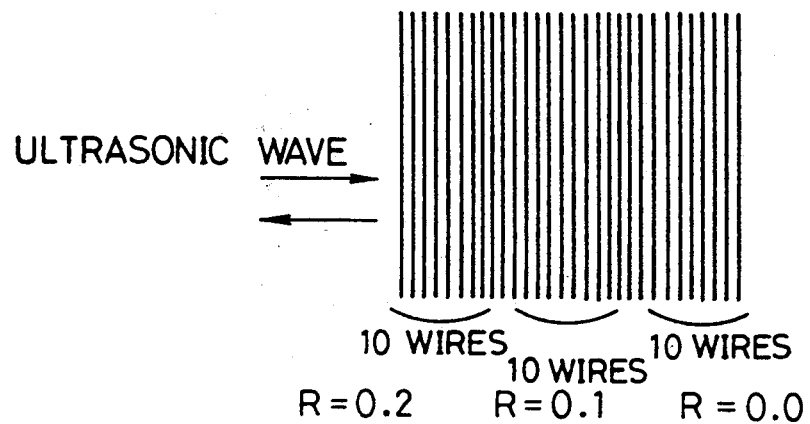
FIG. 6 is a view showing the arrangement of one example of sample.

As shown in FIG. 6, sample 1 was composed of 30 nylon wires which were kept taut, the irregularity of spacing being different at several positions (10 nylon wires per each irregularity of spacing variations). The variations were determined by a normal distribution pseudo-random number, and the variation degree R was defined by the following formula:

$$R = \sigma/\bar{d}$$

where $\sigma$ represents a standard deviation, and $\bar{d}$ represent the average spacing.

The value of R was 0.0, 0.1 and 0.2.

SAMPLE 2

This sample consisting of the group of scatterers had spacing variations at a localized position.

Figure 7:
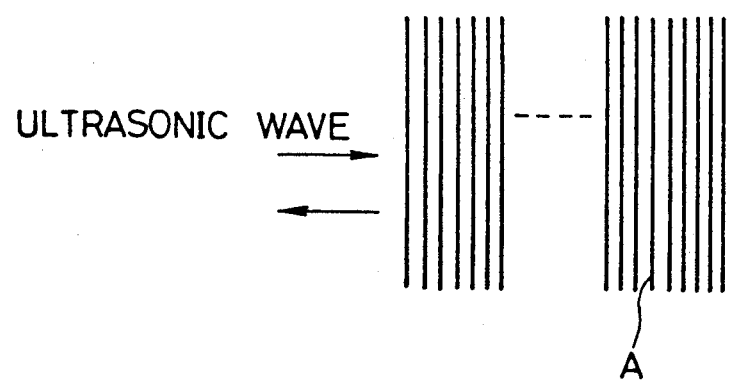
FIG. 7 is a view similar to FIG. 6, but showing another example of sample.

As shown in FIG. 7, sample 2 was composed of 30 nylon wires which were spaced from one another at an equal interval of 2 mm, but the spacing was 2.5 mm at one position indicated by A in FIG. 7.

The results of the measurements will now be described.

MEASUREMENT OF THE SPACE DISTRIBUTION OF THE INTERVAL VARIATIONS OF THE GROUP OF SCATTERS

Figure 8A:
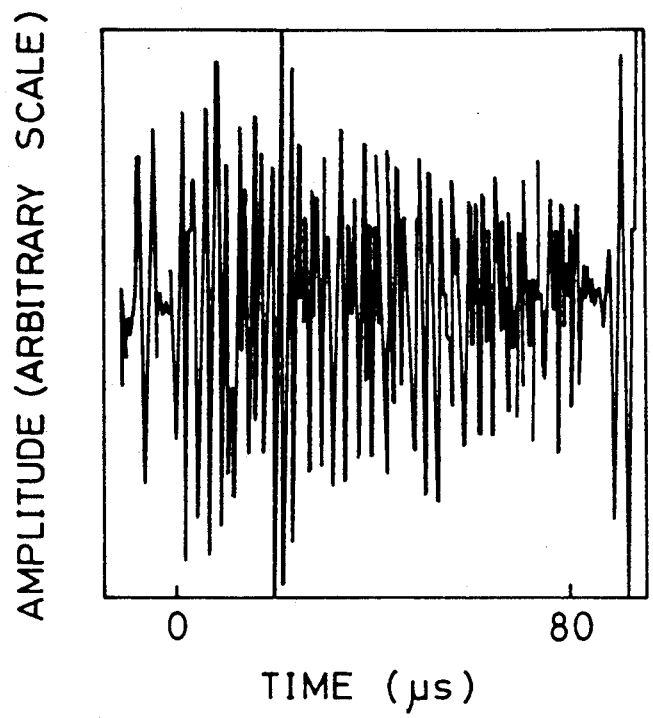
FIG. 8A is an illustration of a waveform of scattered waves reflected from the sample of FIG. 6.
Figure 8B:
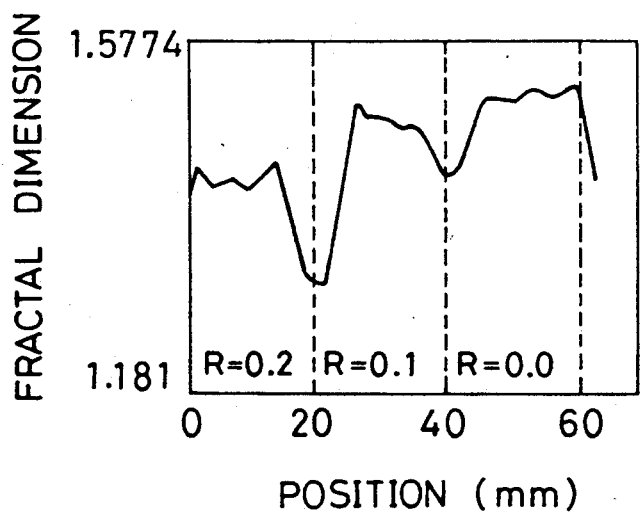
FIG. 8B is a plot showing a fractal dimension of the waveform of FIG. 8A as a function of the position.
Figure 8C:
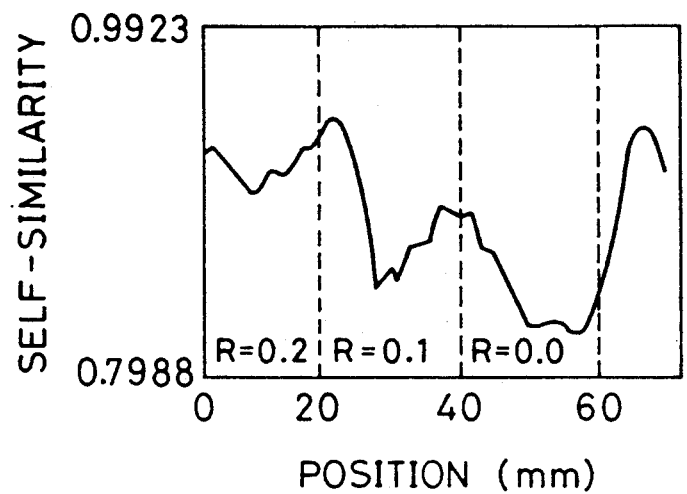
FIG. 8C is a plot showing the self-similarity of the waveform of FIG. 8A as a function of the position.
Figure 8D:
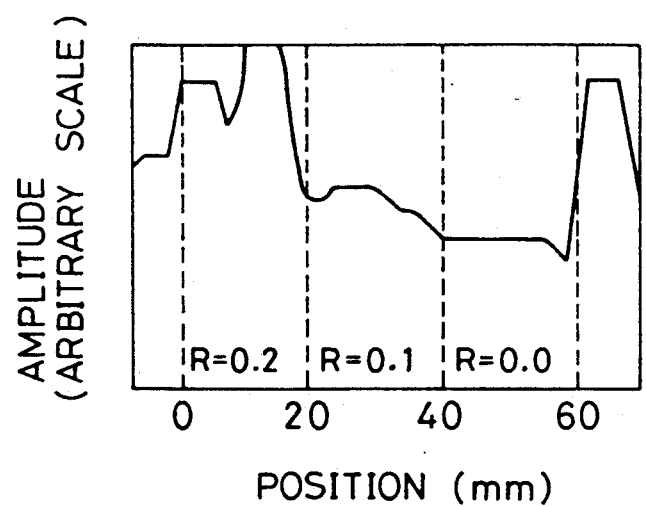
FIG. 8D is a plot showing the amplitude of scattered waves as a function of the position, which is obtained from the waveform of FIG. 8A by a conventional method.
Figure 9C:
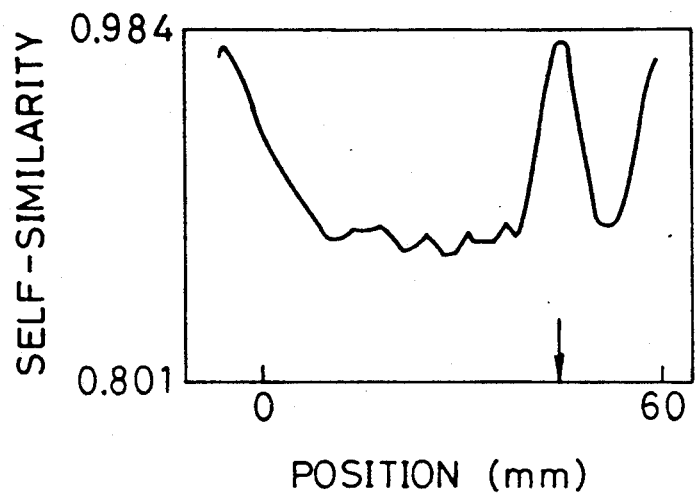
Figure 9D:
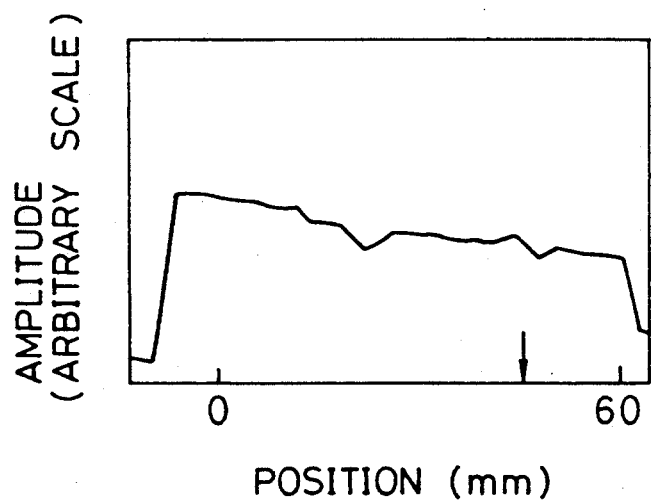

The results of the measurement of the space distribution of the interval variations of sample 1 are shown in FIGS. 8A to 8D. FIG. 8A shows a time waveform of the scattered wave. FIG. 8B is a plot of the fractal dimension as a function of the position. FIG. 8C is a plot of the self-similarity as a function of the position. For comparison purposes, FIG. 8D shows measurement results obtained by the space distribution of a scattered wave amplitude which has already been put into practice as an ultrasonic measurement technique. In FIGS. 8B, 8C and 8D, the extent or range of existence of the sample is between 0 mm and 60 mm.

As shown in FIG. 8D, with the conventional analysis of the scattered wave amplitude, it is difficult to spatially recognize the degree of spacing variations of the scatterers. On the other hand, with the method of the present invention employing the fractal theory, the boundaries between those portions having different degrees of the spacing variations of the scatterers as well as such variation degrees clearly appear, as seen from FIGS. 8B and 8C.

Thus, with the method of the present invention, those regions where the statistical distribution of the spacings between the point scatterers is varied can be clearly recognized.

DETECTION OF LOCALIZED INTERVAL VARIATION

The results of the measurement using sample 2 are shown in FIGS. 9A to 9D. The range of existence of this sample is the same as that of sample 1. In this measurement as in the above measurement, the wavelength of 3 mm and the time window width of 10 μs (corresponding to 7.5 mm in the real space) are longer than the interval between the scatterers, and therefore a sufficient resolution can not be obtained with the conventional time waveform amplitude. This is clear from the time waveform amplitude of the scattered wave shown in FIG. 9D. However, in the fractal dimension (FIG. 9B) and self-similarity (FIG. 9C), a dip and a peak appear at the portion (indicated by arrow in FIG. 9C) where the localized variation in the scatterer spacing occurs.

Thus, in the method of the present invention, even under those conditions in which the scatterer spacing is less than the wavelength of the scattered wave so that a sufficient resolution is not obtained, the localized fine variation in the scatterer spacing can be detected.

While the present invention has been shown and described with reference to a preferred embodiment, it will be understood that numerous modifications, changes, variations and equivalents will now occur to those skilled in the art without departing from the spirit and scope of the invention. Accordingly, it is intended that the invention herein be limited only by the scope of the appended claims.

What is claimed is:

1. A method of measuring a spatial distribution of spacing between point scatterers, comprising the steps of:

applying an ultrasonic wave to an ultrasonic scattering medium which is an aggregation of point scatterers;

converting scattered waves, reflected from said ultrasonic scattering medium, into an electric signal;
determining the shape of a power spectrum of said electric signal;
effecting a fractal analysis so as to determine a fractal dimension and self-similarity with respect to said power spectrum shape; and
measuring a spatial distribution of a structural inhomogeneity of said scattering medium in accordance with results of said fractal analysis.

2. Apparatus for measuring a space distribution of spacings between point scatterers, comprising:
a transmitting/receiving ultrasonic transducer;
means for driving said ultrasonic transducer to cause said vibration to apply an ultrasonic wave to an ultrasonic scattering medium, which is an aggregation of point scatterers, so that said transducer receives scattered waves from said scattering medium and outputs an electric signal representative of said scattered waves;
ultrasonic receiver means for converting said electric signal from an analog form into a digital form;
power spectrum calculating means responsive to a digital output signal from said ultrasonic receiver means so as to calculate the shape of a power spectrum of said scattered waves; and
fractal analysis means for effecting a fractal analysis of said power spectrum shape.

* * * * *